(12) United States Patent
Payrat et al.

(10) Patent No.: US 9,033,948 B2
(45) Date of Patent: May 19, 2015

(54) SINGLE COLLECTION BAG BLOOD COLLECTION SYSTEM, METHOD AND APPARATUS

(75) Inventors: Jean-Marc Payrat, Baulers (BE); Serge Hugard, Jodoigne-Souveraine (BE); Christian Stonig, Ernstbrunn N (AT); Boudewijn Erasmus, Soest (NL); Emmanuel Mignon, Brussels (BE); Christopher D. Gassman, Crystal Lake, IL (US); Clay Little, Lindenhurst, IL (US); Bryan Blickhan, Libertyville, IL (US)

(73) Assignee: Fenwel, Inc., Lake Zurich, IL (US)

(*) Notice: Subject to any disclaimer, the term of this patent is extended or adjusted under 35 U.S.C. 154(b) by 15 days.

(21) Appl. No.: 13/440,051

(22) Filed: Apr. 5, 2012

(65) Prior Publication Data
US 2012/0269679 A1    Oct. 25, 2012

Related U.S. Application Data

(60) Provisional application No. 61/476,955, filed on Apr. 19, 2011.

(51) Int. Cl.
*A61B 19/00* (2006.01)
*A61M 1/02* (2006.01)
*A61M 1/00* (2006.01)

(52) U.S. Cl.
CPC ............ *A61M 1/0272* (2013.01); *A61M 1/0019* (2013.01); *A61M 1/0209* (2013.01); *A61M 2205/6054* (2013.01); *A61M 1/0218* (2014.02)

(58) Field of Classification Search
CPC .. A61J 1/05; A61J 1/10; A61M 1/02–1/0259; A61M 1/36; A61M 1/38

USPC .................................................. 604/403–416
See application file for complete search history.

(56) References Cited

U.S. PATENT DOCUMENTS

| | | | |
|---|---|---|---|
| 5,445,629 A | 8/1995 | Debrauwere et al. | |
| 6,994,790 B2 | 2/2006 | Corbin, III et al. | |
| 7,008,393 B2* | 3/2006 | Robinson et al. | ............ 604/6.01 |
| 7,044,941 B2* | 5/2006 | Mathias et al. | ............... 604/409 |
| 7,703,687 B2* | 4/2010 | Barczyk et al. | ............... 235/492 |
| 2001/0037078 A1 | 11/2001 | Lynn et al. | |
| 2004/0186408 A1 | 9/2004 | Behague et al. | |
| 2008/0274092 A1* | 11/2008 | Godfrin et al. | ............. 424/93.21 |
| 2011/0117647 A1 | 5/2011 | Mayaudon et al. | |

FOREIGN PATENT DOCUMENTS

CH          620830 A5    12/1980

OTHER PUBLICATIONS

European Search Report for EP 12 16 3633 dated Jan. 21, 2013.
Office Action issued in European Patent App. No. 12163633.6 dated Feb. 10, 2014.

* cited by examiner

*Primary Examiner* — Philip R Wiest
*Assistant Examiner* — Benjamin Klein
(74) *Attorney, Agent, or Firm* — Cook Alex Ltd.

(57) ABSTRACT

A blood or blood component collection and processing system, apparatus and method are disclosed. One embodiment includes a vascular access device and a blood collection container having a blood inlet and first and second blood component outlets. The outlets are located at opposite ends of the container, and a blood flow conduit extends between the vascular access device and collection container. The collection container is free of attachment to other blood collection containers when in an initial collection configuration at the time of collection.

11 Claims, 6 Drawing Sheets

SINGLE COLLECTION BAG BLOOD COLLECTION SYSTEM, METHOD AND APPARATUS

CROSS REFERENCE

This application claims priority from and the benefit of U.S. patent application Ser. No. 61/479,955, filed Apr. 19, 2011, which is incorporated by reference.

FIELD

The present invention relates generally to blood collection systems, apparatus and methods for collecting and processing blood.

BACKGROUND

It is well known to collect blood from donors in pre-assembled and pre-sterilized blood collection systems. Such systems typically include a primary collection container and at least several separate satellite containers interconnected with associated flexible tubing, flow control devices and filters, as desired. Such systems may also include blood cell preservatives and other solutions. Typically, whole blood is drawn into the primary collection container through a vascular access needle. After collection, the entire system, including primary container, satellite containers, fluid flow tubing, flow control devices and filters, is placed into a centrifuge and the entire assembly is subject to centrifugation. During centrifugation, the blood in the primary collection container separates by reason of the different density of the blood components, into more dense concentrated red blood cells at one end of the container and lighter plasma toward the other end of the container, with an intermediate layer, sometimes referred to as buffy coat, which may comprise leukocytes and platelets.

Following centrifugation, the plasma is expressed through flow tubing and into a plasma collection or first satellite container. Also, a leukocyte reduction filter may be provided in the fluid flow tubing so that any leukocyte population in the plasma is reduced as the plasma is expressed into the plasma collection container. The plasma collection container may then be sealed and severed from the remainder of the system for subsequent administration to patients or later processing as a fresh frozen plasma. If the centrifugation is carried out at sufficiently low speeds or time so as to allow substantial numbers of platelets to remain in the plasma, the collected plasma may be subject to further centrifugation for separation into platelet-poor or platelet-depleted plasma and platelet concentrate. During such centrifugation, the platelet-poor plasma accumulates toward one end of the plasma collection container and the platelet concentrate collects toward the other end of the plasma collection container. The platelet-poor plasma may then be expressed from the first satellite container into a second satellite container for storage, administration to patients or subsequent processing. A platelet preservative may be added to the platelet concentrate remaining in the first satellite container to enhance viability during storage. The remaining red blood cell concentrate in the primary container may be stored there or be expressed into other satellite containers and combined with a red cell preservative solution to extend the storage life of the red cells.

If the centrifugation of the primary container is at sufficiently high speed or for sufficiently long time, platelets may be forced into the intermediate cell layer (buffy coat). In that situation, typically the plasma will be expressed from the primary container leaving the buffy coat and red cells in the container. The red cells may be expressed from the primary container, allowing the buffy coat layer to remain therein, or the remaining contents may be agitated to mix the platelets and leukocytes with the red cells, which may remain in the primary container or be expressed to another container.

Although blood collection systems such as that described above offer significant advantages in terms of user convenience, the manufacturer of such systems can be relatively complex and the systems can be relatively expensive. This can present a drawback in the event the system must be discarded before it is fully utilized. For example, it may be determined after collection that a particular donor was not qualified to provide a blood donation, in which the event the entire blood component collection system with all the associated containers, flow control devices and filters will need to be discarded.

It has been suggested to address these issues by collecting blood from a donor into a system having a single container, leaving subsequent processing in the hands of other trained personnel associated with the blood bank or collection agency, who can manipulate and process the collected blood in a manner desired at that time. (U.S. Pat. No. 6,994,790). Although, this approach may be useful in certain circumstances, there continues to be a need for new systems, apparatus and methods that advance the efficiency of blood collection and processing and provide other benefits.

Such advances are provided in significant part by the subject matter of this description and the associated drawings accompanying it.

SUMMARY

Various aspects of the present subject matter are set forth in the written description, drawings and claims below. By way of summary of a few of those aspects, one implementation or aspect of the present subject matter is found, in general, in a blood collection system. The blood collection system, in a collection configuration, comprises a vascular access device for drawing blood from a donor or patient; a blood collection container including a blood inlet and having opposed ends, one end of the container including a first blood component outlet and the opposed end of the container including a second blood component outlet, and a blood flow conduit extending between and in fluid communication with the access device and the blood inlet of the blood collection container, with the blood collection container being free of attachment to other blood component collection containers receiving blood components from the collection container.

In another implementation or aspect, the above blood collection system could be configured for collection of bone marrow or blood from an umbilical cord after birth for subsequent processing or storage. Such a system could employ a collection container having a single fluid flow port or ports at opposed ends of the container as described above. Such a system may employ a needle, needleless access or other form of access device for accessing bone marrow or cord blood. The container may optionally be later sterile connected to other processing apparatus or subassemblies, such as described below, for concentration of mononuclear cells, addition of cryoprotectant, etc.

In another implementation or aspect a blood processing assembly is provided comprising a blood collection subassembly, a plasma collection subassembly, and a red cell collection subassembly; the blood collection subassembly comprising a blood collection container having a closed blood inlet and having opposed ends, a plasma outlet and a red cell outlet; the plasma outlet being connected by a sterile connection union to the plasma collection subassembly and the red cell outlet being connected by a sterile connection union to the red cell collection subassembly; and the red cell collection subassembly comprising a red cell collection container and a red cell flow conduit communicating between the red cell collection container and through the sterile collection union with the red cell outlet, a processing container located in fluid flow communication with the red cell flow conduit between the sterile connection union and the red cell collection container, wherein the red cell collection container contains certain ingredients of a red cell preservation solution and wherein the processing container contains other ingredients of the red cell preservation solution.

In another implementation or aspect, a method is provided for collecting one or more blood components comprising collecting whole blood from a donor into blood collection container or providing a collection container of pre-collected whole blood, the collection container including a blood connection inlet and opposed ends, one end of the container including a first blood component outlet and the opposed end of the container including a second blood component outlet, the blood collection container being free of attachment to other blood component collection containers during the collecting or providing; centrifuging the blood collection container sufficiently to separate the collected blood into at least a plasma component disposed toward the one end of the container and a concentrated red component disposed toward the other end of the container; sterilely connecting a plasma collection subassembly including a plasma collection container in fluid communication with the first blood component outlet and/or a red cell collection subassembly including a red cell collection container with the second of the blood component outlet; and expressing the plasma component and/or the concentrated red cell component from the collection container into the respective subassembly.

These are only some of the implementations or aspects of the present subject matter, and may be used alone or with other features and aspects as set forth below.

DESCRIPTION

Figure 1:
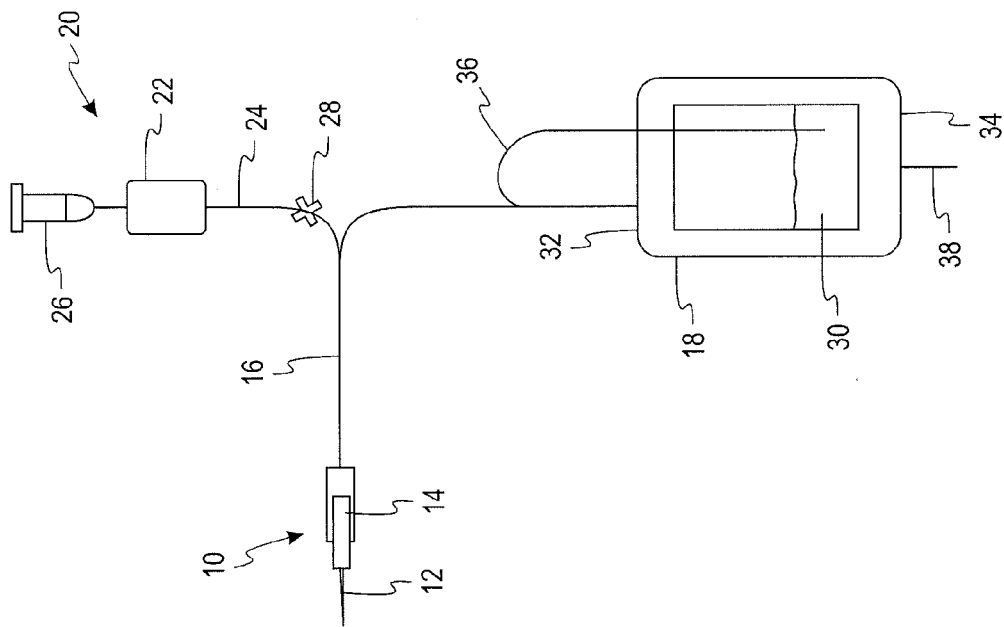
FIG. 1 is a plan view of a blood collection system in accordance with one aspect of the subject matter described herein.

Turning now to a more detailed description of the figures, FIG. 1 is a schematic plan view of a blood collection system that includes a donor access device 10, which may typically but not necessarily include an access needle 12 and needle hub 14, in fluid communication with a flexible plastic blood flow tubing 16 which extends from the needle or other access device to a primary blood collection container 18. An exemplary pre-donation sampling system, generally at 20, is also illustrated as part of the blood collection system 10. The pre-donation sampling or collection system 20 is shown for purposes of illustration and not limitation and is an optional aspect of the present subject matter. As illustrated, the pre-donation sampling system includes a sample container or pouch 22 which is connected to the blood inlet flow tubing 16 at tubing branch connector or Y-site 24. The sample collection container 22 is accessible by a syringe or standard vacuum sampling system, generally illustrated at 26, for withdrawing a blood sample from the sample container or pouch 22. As is well known in the field, blood first removed from a donor is directed into the sample pouch for appropriate sampling to qualify the blood or blood component for further administration or processing. In addition, any skin plug formed by the needle puncture and associated skin-based contamination or bacteria is also flowed into the sampling container 22, thereby reducing the potential bacterial load of blood subsequently collected into the primary collection container 18. For purposes of the description, the sample pouch 22 is not considered a blood or blood component container.

After the blood sample was collected, the branch tubing 24 is closed or sealed, as at 28, and the blood withdrawn from the donor is directed into the primary collection container 18. The primary collection container preferably is pre-filled with an amount of anticoagulant 30, such as CPD, to prevent blood clotting, or anticoagulant such as CPD or ACD could be added later, such as during collection. As illustrated, the collection container 18 has opposed end portions 32 and 34, and the blood flow tubing 16 extends from the patient access device 10 to the container and enters the container at the first end portion 32 of the container. For enhancing the mixing of blood with anticoagulant, the illustrated system includes a tubing loop 36, one end of which is connected at a fluid junction with blood tubing 16 and the other end of which extends through first end 32 of the container and into the container, terminating nearer to the second end portion 34 of the container but spaced therefrom. Preferably the internal end of the tubing loop 36 extends into the anticoagulant and, as will be described in more detail later, a pump may be associated with the tubing loop for drawing the anticoagulant from the container 18 and mixing it with whole blood flowing through tubing 16 as it enters the container. This circulation may be continued throughout the blood collection process to gradually and thoroughly mix the anticoagulant with the whole blood withdrawn from the donor. After the initial collection of a desired amount of whole blood, e.g., 450 cc, either the inlet flow tubing flow 16 and/or a portion of the tubing loop 30 may be sealed and severed. The portion of either tubing remaining attached to the container may later be used for withdrawing a blood component from the container. Alternatively or additionally, a separate blood component collection outlet tube may be provided that extends from the first end 32 of the container 18. As illustrated, second end portion 34 of the container 18 includes a blood component outlet tube 38 that is in a closed or sealed condition during the initial collection process, when whole blood is being withdrawn from the donor and introduced into the primary collection container 18.

Figure 2:
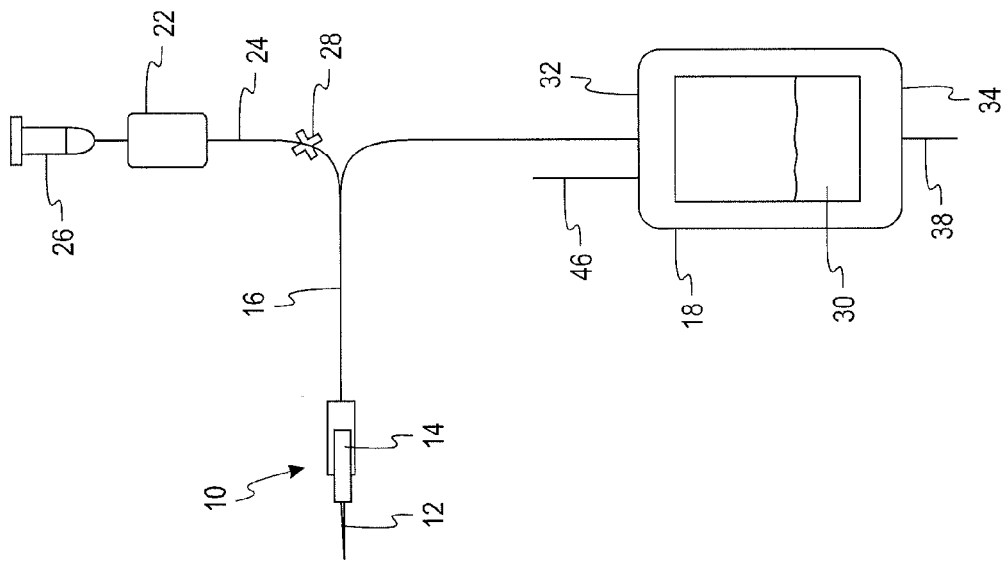
FIG. 2 is a plan view of a blood collection system in accordance with another aspect of the subject matter described herein.

The blood collection system in FIG. 2 has substantially the same features and functions as the blood system in FIG. 1 and is numbered similarly—except that the blood collection system in FIG. 2 lacks the tubing loop 36. In both the FIG. 1 and FIG. 2 blood collection systems, it is to be noted that there are no satellite containers or bags for receiving any blood components from the primary collection container. The relatively small container 22 of the pre-donation sample collection system 20 (e.g. <50 cc) receives blood directly from tube 16 and not from the collection container 18, and is not regarded as a satellite container. Also, the pre-donation sample system is usually sealed and disconnected from the system after the sample is collected and before further processing, and is not considered a satellite container as referred to herein.

Figure 3:
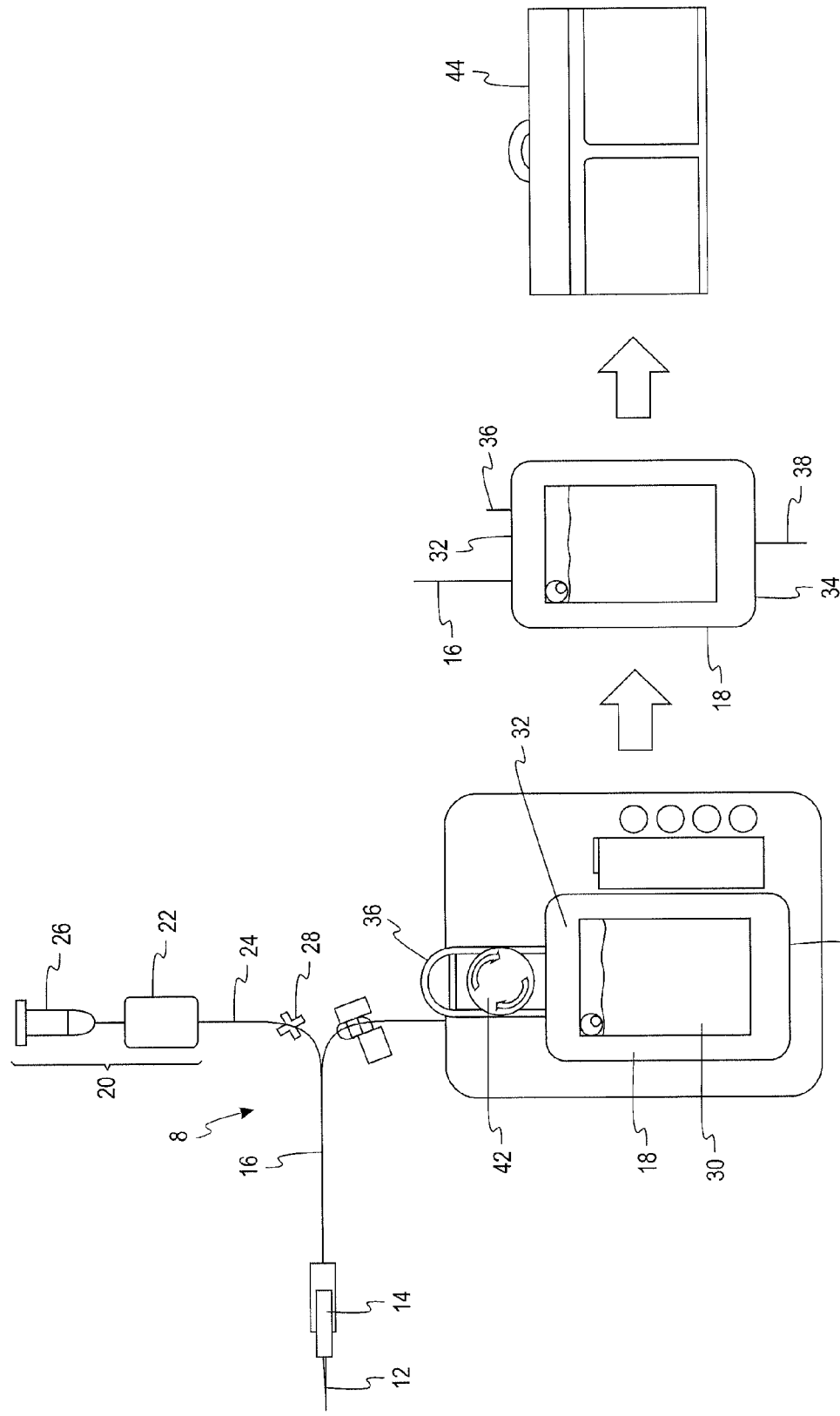
FIG. 3 illustrates the blood collection system of FIG. 1 during the blood collection process from a donor, with a flow diagram illustrating subsequent blood processing steps.

Turning now to FIG. 3, FIG. 3 illustrates the blood collection system 8 of FIG. 1 mounted on a mixing pump device, generally at 40 for enhancing the mixing of the whole blood withdrawn from the donor and the anticoagulant within the primary collection container 18, such as CPD or ACD or other anticoagulant 30. As illustrated in FIG. 3, the illustrated pump 40 includes a peristaltic rotor 42 that cooperates with the tubing loop 36 and the blood flow tubing 16 to draw anticoagulant from the primary collection container 18 and mix it with the incoming whole blood flow through tubing 16. Other types of pumps could also be used. The pumping preferably continues throughout the collection process whereby the pump continuously draws anticoagulant or anticoagulant/whole blood mixture from the container 18 and adds it to the whole blood entering through tubing 16. With this arrangement the anticoagulant can be gradually added to the incoming blood in a metered process that, upon completion of the blood collection process, provides a fully mixed combination of blood and anticoagulant within the primary collection container 18. The pump may include rate controls, allowing the user to select the pumping rate at which the anticoagulant is combined with the incoming whole blood. After the blood processing selection is complete and a unit of whole blood is collected within the primary collection container 18, the inlet tubing 16 and optionally the tubing loops are sealed and severed. The primary blood collection container 18 is removed from the pump and placed in a transportation container 44, which may be conditioned by cooling if desired to maintain the blood at a desired temperature while it is transported away from the collection area to a processing station (sometimes called a Back-Lab). The processing station may be on the same premises where the blood is collected or, more typically, at a more distant location where incoming collected blood from various locations is identified, sorted and processed further, based on blood component demands and blood type.

Although FIG. 3 illustrates the blood collection system 8 of FIG. 1, employing a mixing pump, it should be noted that an alternative is to employ the blood collection configuration as illustrated in FIG. 2 which collects blood from the donor directly into the primary collection container 18 without a mixing pump or other arrangement. In that configuration, the anticoagulant in container 18 may be mixed with the inflowing blood by manual manipulation of the primary collection container during the collection process. Similar to the processing that was described above, at the end of the collection process employing the system of FIG. 2, the blood collection tubing 16 is sealed and severed and the filled container 18 may then be placed in the transportation container 44 for transport to the processing station. For purposes of illustration, and not limitation, the primary collection container 18 shown in FIG. 2 is illustrated with a blood component outlet 46 located at the first end 32 of the collection container. As noted before, the remainder of the blood inlet flow tubing 16 connected to the container end 32 after the tube is sealed and severed may also be used as a blood component outlet, and an additional outlet such as outlet 46 may not be required. In other words, the same access point into the primary blood collection container 18 may function as a blood inlet during blood collection and as a blood component outlet after collection. The blood inlet and outlet tubing of any of the figures above may include an internal frangible seal or closure (e.g., a frangible cannula) that may be broken and opened by external manipulation of the tubing, such as by bending the tubing. Such frangible closures are well known in the field.

After the primary collection container 18 is severed from the remainder of the blood collection system and sealed, as noted above, it is placed in a transportation container 44 which may be a closed environmentally controlled container, open racks or other transportation systems for conveying to a remote blood processing station. By "remote," it is meant a blood processing station that is not also the blood collection station but separate from the blood collection station. It may be in the same facility, even in the same room, or at a completely different facility. Typically the blood processing facility will be manned by personnel knowledgeable of any particular blood component needs and familiar with the more detailed and complicated procedures for subsequent blood processing.

Figure 4:
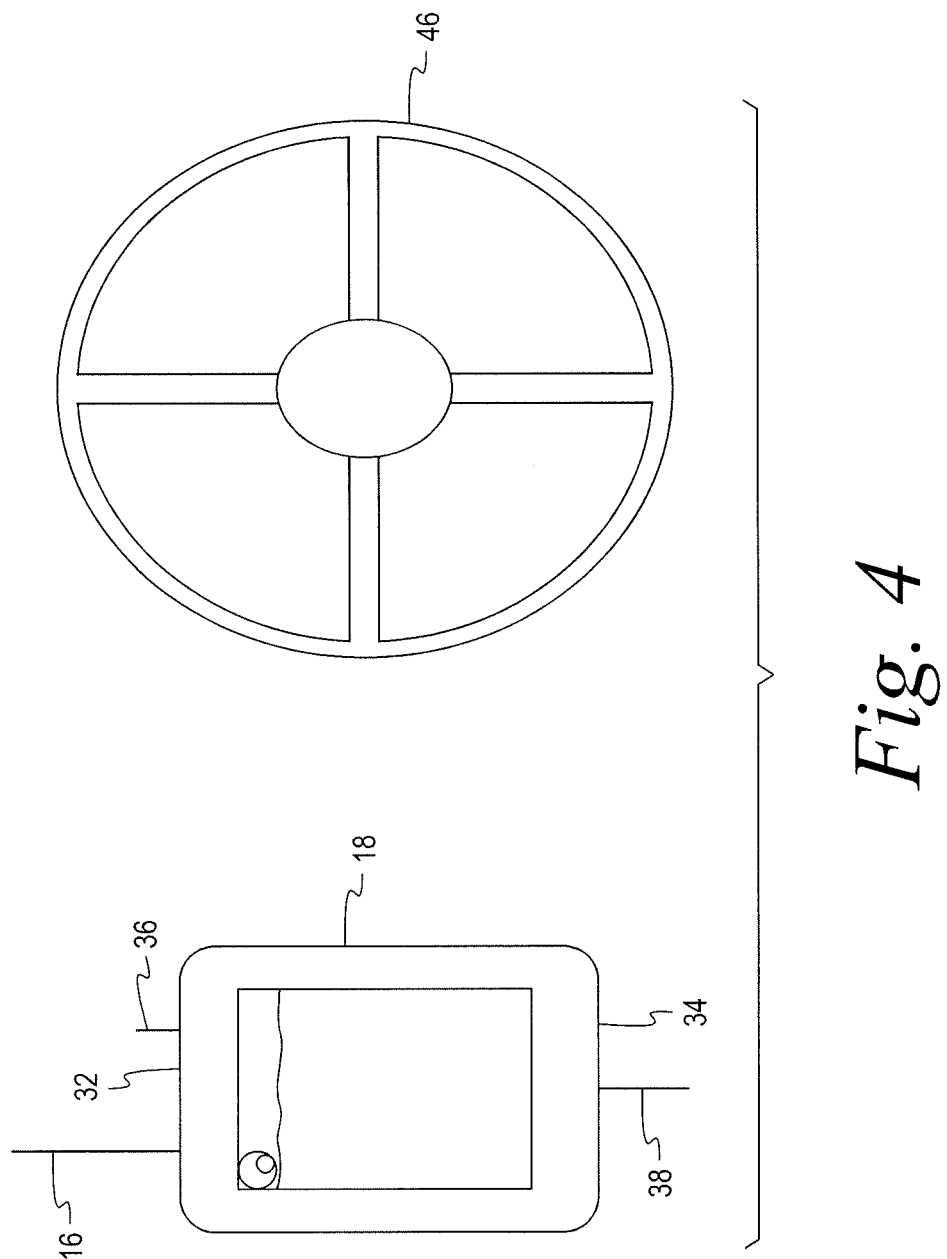
FIG. 4 illustrates still further processing steps after the steps of FIG. 3 including centrifugation in a centrifuge device.

In accordance with present subject matter, the single blood collection units of FIGS. 1 and 2, after transport to the blood processing station, are first subjected to centrifuging or other exposure to a centrifugal force field, such as by placing the units in a rotary centrifuge 46, as illustrated in FIG. 4. The rotary centrifuge may have individual compartments or "buckets" each of which is sized to receive a filled primary collection container. The centrifuge may have a plurality of stations or buckets for processing (spinning) numerous collection containers simultaneously.

Although it is contemplated that at least initially, the blood collection containers 18 can and will be manually loaded into the centrifuge 14, the use of a single collection container without associated tubing, satellite containers, filters and the like complements automation of the centrifuge loading process. Automation may include associated conveyor or robotic systems that are configured to retrieve the filled primary collection containers, place them in the appropriate station or bucket of the centrifuge device, and performing that action repeatedly until the centrifuge device is full, at which time the automated system may be programmed to begin the centrifugation process at such speed and time as may be selected by the operator depending on the subsequent processing to be employed. After centrifugation is complete, the automated or robotic system may remove the containers from the centrifuge and transport them to the next processing stage.

As pointed out earlier, the centrifugation causes density separation of blood components within the primary collection container 18 with the relatively denser red cell component accumulating at the lower or the radially outer end of the container and the lighter plasma accumulating at the upper or radially inner end of the container. Depending on the speed of the centrifuge and the cycle time, an intermediate layer comprising white cells and platelets may also be provided during the centrifugation. This layer is commonly referred to as the buffy coat. The present subject matter is not limited to any particular centrifugation cycle or speed, and the primary collection container may be subjected to a centrifugation cycle (sometimes called a low speed or "soft spin") that allows many of the platelets to remain within the plasma, creating what is often referred to platelet rich plasma, or a high speed or "hard" spin that creates platelet poor plasma, red cell concentrate and buffy coat therebetween. The platelet rich plasma may be subsequently subjected to further centrifugation, as will be described later, for separating concentrated platelets from platelet-poor or platelet-reduced plasma. Similarly, the red cell concentrate in the collection container 18 may be expressed to a red cell container or processing subassembly. If a hard spin is used, the buffy coat may be allowed to remain in the collection container, or alternatively, the buffy coat and red cells may be remixed and the combination red cell concentrate and buffy coat layer expressed to a red cell collection subassembly for further processing. Of course the automation described above may be suitable not only for loading the primary collection containers into the centrifuge and operating the centrifuge but also may be employed for removing the primary collection containers from the centrifuge after the centrifugation is completed.

Figure 5:
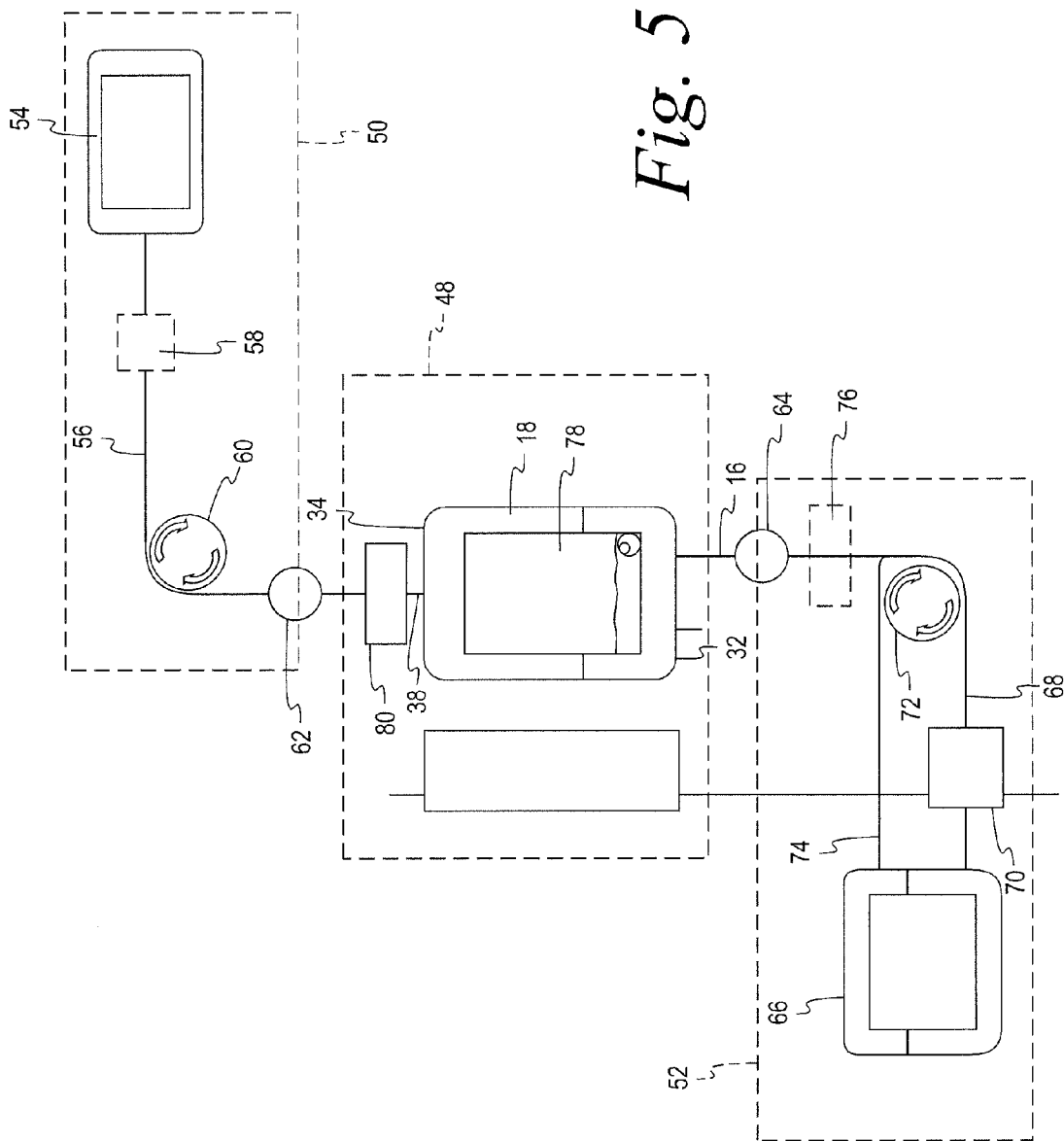
FIG. 5 is a schematic plan view of a blood collection system including a blood collection container in accordance with another implementation or aspect of the present subject matter attached by sterile connection unions to a plasma collection subassembly and to a red cell collection subassembly for further processing.

FIG. 5 illustrates the particular primary collection container 18 (after centrifugation) mounted for subsequent processing. More specifically, the blood components (plasma and red cells) are located at opposite ends of the container 18 due to the centrifugation, and the collection container 18 may be mounted on a device which expresses the blood components from the collection container, either manually or automatically, as desired. As illustrated the primary collection container is mounted with the red cells lowermost and the plasma uppermost in the container. One example of such device for expressing the contents from their respective end of the container is the Optipress™ component extraction device 48, sold by Fenwal, Inc. of Lake Zurich, Ill., and another is the so-called Archimedes device which may look like the device in FIG. 6. Prior to or after mounting in association with the extraction device 48, the primary collection container 18 may be attached to a plasma collection subassembly 50. More specifically, the illustrated plasma collection subassembly 50 includes one or more plasma collection or processing containers 54, a plasma flow conduit, such as plastic tubing 56, extending from the plasma collection container 54 and, if desired, an optional leukocyte reduction filter 58 that may be provided in the plasma flow path for filtering plasma before it enters the plasma collection container 54.

The plasma subassembly 50 may include or be mounted on hardware or other apparatus optionally including an associated pump, such as rotary peristaltic pump 60, for drawing or assisting in drawing plasma from the primary collection container and passing it through a leukocyte reduction filter 58 under pressure. Although illustrated as a peristaltic pump, other types of pumps may be used, and one or more portions of the system illustrated in FIG. 5 may be in a form of a flow control cassette, with one or more pre-formed passage ways that are controlled by a reusable controller for controlling the pump rate and direction of fluid flow through the plasma collection subassembly. The plasma collection subassembly is, accordingly, a separate and independently useful aspect of the present subject matter.

The plasma collection subassembly 50 is, as noted earlier, not pre-attached to the primary collection container 18, but instead is preferably attached by a sterile connection union 62 which joins the plasma collection tubing 56 to outlet tubing 38 extending from, for example, the upper end 34 of the collection container. There are a variety of devices for forming such connections in a sterile fashion. The present subject matter is not limited to the use of any particular design or configuration of sterile connection device. One example of a well know sterile connection system is the so-called Sterile Connection Device, which employs heated wafers to simultaneously melt and join the plastic tubing of different components in a sterile manner (See, e.g., U.S. Pat. No. 4,443,215).

In addition, the primary collection container 18 may be connected, by a similar sterile union 64, to a red cell collection subassembly 52. As illustrated this subassembly includes one or more red cell collection or processing containers 66 and a fluid conduit such as flexible plastic red cell collection tubing 68 extending from the red cell collection container 66 to the sterile union 64, which connects the tubing 68 to tubing 16. The tubing 16 earlier functioned as the whole blood inlet tubing into the collection container 18 and in the FIG. 5 configuration now functions as a blood component outlet or collection tubing, with the red cell collection tubing 68 being in fluid flow communication with the red cell collection container 66 at one end and with the blood component outlet tubing 16 at the other end. The red cell collection subassembly may include a leukocyte reduction filter 70 for reducing the leukocyte population in the red cell concentrate expressed from the lower end of container 18.

To enhance storage of the red cells, and accelerate filtration rate, red cell collection subassembly may include a tubing branch 74 extending between the red cell collection container 66 and the red cell collection tubing 68, forming a tubing loop that is cooperative with an optional pump 72 for circulating red cell preservative solution from the red cell collection container 66 into the red cell collection 68 for mixing with the red cell as they are withdrawn from the primary collection container 18 and passed through optional filter 70. Continued operation of the mixing pump 72 as red cells are withdrawn from the primary collection container 18 results in more complete mixing of the red cells with the preservative. In addition, it is optionally contemplated that the red cell collection subassembly may include a processing container, diagrammatically illustrated in the drawing as container 76 downstream of the sterile union 64.

The use of a separate blood cell collection subassembly also permits the potential use of non-PVC materials for red cell storage, in contrast to materials commonly found in blood collection systems currently. Non-PVC materials are often more fragile and frangible than PVC and insufficiently durable for high speed centrifugation of the type employed in blood cell separation, as described above. One type of non-PVC material may be polyolefin or other suitable non-PVC material that is biologically compatible and suitable for sterilization and storage of red cell preservative solution and red cell concentrate. One such non-PVC material that may be considered for this application is material PL2411 from Fenwal, Inc. from Lake Zurich, Ill.

Further, having two containers 66 and 76 as part of the red cell collection subassembly has particular advantage in connection with the use of a red cell preservative that may require a combination of ingredients packaged in separate containers. More specifically, for red cell preservative solution such as Erythro-Sol from Fenwal, Inc. of Lake Zurich, Ill., as described in U.S. patent application Ser. No. 12/888,962 filed Sep. 23, 2010, incorporated by reference, the red cell preservative includes glucose in one container and other red cell preservative ingredients in another container (for separate sterilization), which ingredients must be mixed together. As illustrated, the glucose may be contained (pre-filled) in the red cell collection container 66, and the other ingredients contained in the processing container 76 (or vice versa). Red cells from the primary collection container could be flowed, if desired with the assistance of pump 77, into container 76 and from container 76 through the leukocyte reduction filter 70 (if desired) and into the red cell collection container 66 wherein the red cells and preservative ingredients from container 76 are mixed with the glucose in the red cell collection container 66. Although not required for the subject matter of this description, the mixing pump 72 aids in mixing the various ingredients of the red cell preservative solution with the red cells being withdrawn from the primary collection container 18, while also accelerating the leukocyte filtration by forcing flow of the blood cells through the red cell filter 70 under pump pressure.

The red cell collection subassembly as illustrated with two containers also allows the red cell preservative solution in the container 66 to be used for priming or wetting of the filter media in the leukocyte reduction filter 70 which can be advantageous to enhancing the filtration speed and quality of the red cell filtration process. Thus, the red cell collection subassembly is also a separate and independently useful aspect of the present subject matter.

The plasma collection subassembly and the red cell subassembly may be provided as preassembled disposable fluid tubing and container sets suitable for mounting on an appropriate durable reusable hardware device, which may contain pump rotors such as 60 and 72 or other suitable pumping arrangements if desired. Alternatively, one or both of the plasma collection subassembly and the red cell collection subassembly may be provided in more compact integrated form, employing flow control cassettes with pre-formed passageways and, if desired, pumping tubing loops and/or diaphragm pumps to control the flow of fluid through the respective collection subassembly. More specifically, such cassettes may employ a durable programmable controller upon which the cassettes or preassembled tubing and bag systems or subassemblies are mounted, with associated flow control features which allow automatic flow control of the plasma and/or red cells into and through the respective subassembly. Such a controller may be free standing or may be combined as a unit with the extraction device 48.

The employment of preassembled integrated devices in the configuration of a compact, self-contained module particularly with a cassette remote control system may also permit the use of automatic or robotic loading of the red cell collection and the plasma collection subassemblies onto associated hardware or controller systems. It is also contemplated that such an automated system may include a sterile docking module which automatically forms either separately or simultaneously the sterile connection unions 62 and 64, connecting the primary collection container 18 with the plasma and/or red cell collection subassemblies. And the plasma and red cell subassemblies may be configured or integrated as part of a single larger assembly for automated mounting. Such an automated system may also include an electronic or optical reader for reading the donor, blood type or other information contained on a label 78 on the primary collection container and printing new labels with the appropriate data accurately transferred onto the new labels for adhering onto the plasma container 54 and/or the red cell concentrate container 66.

The system illustrated in FIG. 5 also has particular benefits for applications in Europe or other locals where different collection techniques are provided for buffy coats. As noted earlier, the centrifugal separation of the blood components within the primary collection container may result in the lighter plasma moving toward one end of the container, the denser red cells moving toward the other end of the container and the intermediate density white cells and platelets forming the buffy coat layer between the plasma and red cells. In Europe it is common to treat the buffy coat collection in one of at least two different ways. For example, the buffy coat may be allowed to remain in the primary collection container 18 and only the plasma and concentrated red cells expressed from the container 18. Alternatively, the plasma may be expressed from the container 18, after which the primary collection container 18 is agitated to remix the buffy coat layer with the red cells. The combination red cell concentrate and buffy coat layer are then expressed from the primary collection container. The system illustrated in FIG. 5 accommodates either of those approaches and may be automated through a main controller to carry out the desired extraction procedure automatically as selected by the user.

The illustrated extraction system in FIG. 5 may include an optical sensor 80 along the blood component outlet flow path 38 which detects the entry of red cells into the blood component collection 38. Since plasma is to be collected through that line in the illustrated embodiment, when the optical sensor detects the present of red cells, it can signal to the extraction device and/or other controller that all of the plasma has been expressed from the container 18 and stop the pump 60 and close any associated valve or clamp on the plasma flow lines 56. Of course, the extraction device and any other controller may include a user interface, such as keyboard, touch screen, or a data entry pad to communicate information to the user and/or allow user entry of the desired process to be carried out.

Figure 6:
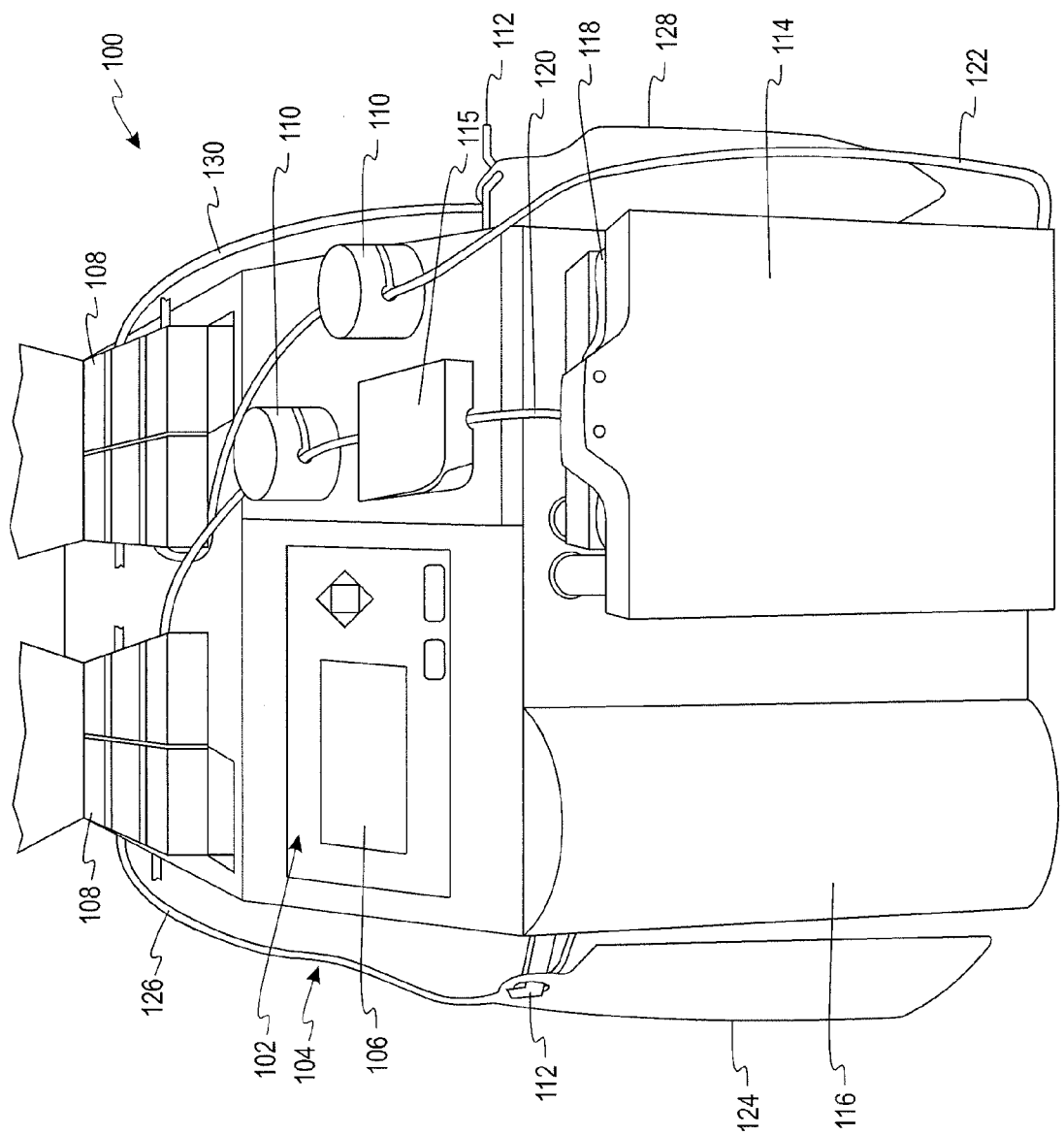
FIG. 6 is an elevational view of a blood collection system in accordance with another aspect of the present subject matter.

FIG. 6 is a view of another blood collection system, generally at 100. As shown there, the system includes a durable or reusable hardware component 102 and a disposable component or portion 104. The hardware component has various integrated features and includes, among other features, an optional user interface 106, at least one and preferably two or more sterile connection devices 108, tubing clamps and/or heat sealers 110, one or more hangers 112 optionally associated with a weight scale, a compression arrangement such as a press plate 114, for expressing contents of a container, an optional wireless/communication module or subassembly 116 and an optional hemoglobin detector 115. The device preferably includes an integrated controller for commanding operation of the device, monitoring conditions and providing instructions, prompts and/or warnings to the user.

The illustrated disposable system used with hardware includes a primary collection container 118 with associated plastic tubings 120 and 122 communicating at opposite ends of the collection container, a plasma container 124 with tubing 126 and a red cell container 128 with tubing 130. The tubings are mounted in the sterile connection devices 108 for automated formation of sterile connection unions between the tubing 120 from the top of the primary container and the tubing 126 of the plasma container and between tubing 122 from the bottom of primary container and the red cell tubing 130. As illustrated, the plasma container is supported on a weight scale hanger 112 and the tubing 120 extends through the hemoglobin detector 115 to detect the presence of unwanted red cells or hemoglobin in the plasma expressed from the primary container.

The press plate 114 is mounted to selectively compress the primary container 118 as desired to express plasma and/or red cells alternatively or simultaneously. In one embodiment, the press plate may be hinged at the bottom to form a V-shaped receiving station or slot for the primary container and may be pivoted mechanically, hydraulically or pneumatically to compress the primary container. The clamps 110 may be operated in cooperation with the press plate to allow expression of the desired blood component and to seal and sever the tubing by heat or radio frequency seal after expression.

Figure 7:
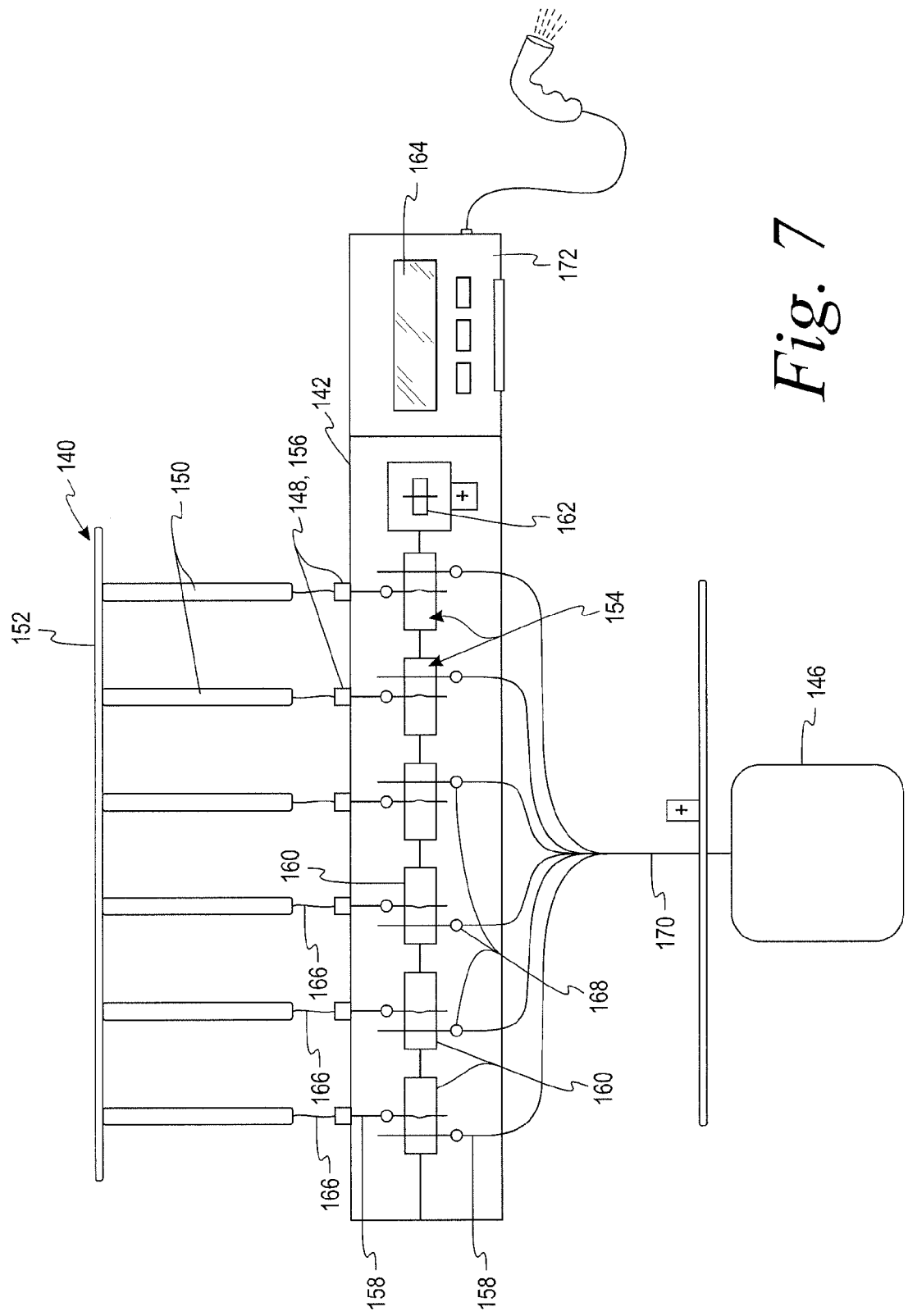
FIG. 7 is a plan view of another sterile connect device or system that may be used for connecting or manifolding a plurality of containers in accordance with another aspect or implantation of the present subject matter.

FIG. 7 shows a blood or blood component processing system for connecting/manifolding or pooling two or more blood component containers and that may be used with the various embodiments described herein. The illustrated pooling system includes a blood or blood component collection source container suspension apparatus 140, a multi-station sealing fixture 142, a fluid flow manifold or pooling flow circuit or set 144, a pooling container 146 and associated sealing head 148. The system is operable for combining or pooling blood or blood components from multiple source containers 150 into the pooling container 146. The system can be used for any number of source containers, preferably from two to six or more.

The suspension apparatus is shown for purposes of illustration as a horizontal container or bag holding support member 152 that has a plurality of spaced apart suspension or hanging locations, which may in the form of hooks or clamps, that suspend the containers vertically over the fixture 142 such that each container is associated with one of the plurality of functional stations 154 located on or in the fixture 142.

For purposes of illustration, the suspension apparatus 140 and support member 152 are shown for hanging six source collection containers 150 in general registration with six functional stations 154 of fixture 142. More or fewer source containers and/or stations may be used.

Each functional station 154 of the fixture 142 preferably includes frangible cannula opener or cracker 156, a sealing head (which may be part of the opener or separate from the opener), tubing guides 158 and sterile connection site 160. The illustrated fixture 142 also includes a sterile connection module 162, an optional integrated or separate user interface 164 and scanner 166.

More specifically, each illustrated source container 150 has flow outlet conduit or tubing 166 extending from the container. The tubing may include an internal frangible closure (not shown) that normally seals the conduit and is openable by external manipulation or bending of the tubing to break the frangible internal closure. Such frangible closures are well known in the medical field. The outlet flow conduit or tubing 166 of each source container 150 is associated with the cannula opener 156 and sealer in one of the functional stations 154 of the fixture 142.

For pooling the contents of the source containers 150, the manifold flow set 144 includes a plurality of sealed inlet tubes 168 that join or flow into single outlet conduit or tube 170, which is in communication with the destination or pooling container 146. Each sealed inlet tube is associated with one of the functional stations for joining with outlet tubing 166 of the respective source container 150 at that station.

The source container outlet tubing 166 and manifold inlet tubing 168 are positioned within tube guides, e.g. slots, that cooperate with the sterile connection module 162. The tubing or conduits are preferably made of a thermoplastic material, such as PVC, and any suitable sterile connection system may be used, including the device described earlier that uses heated wafers to slice the tubing, and tubing guides that slide the molten ends of the tubing together without exposing the interior of the tubing to ambient contamination. The illustrated fixture 142 employs a single sterile connection module 162 that can be moved into association with each of the functional stations, as desired. Of course, each station could also have its own sterile connection module if so desired. Non-PVC tubing could also be used if non-PVC sterile connection systems are available.

The system may also have a built in pressure test facility for testing the integrity of a sterile connection before opening the source container conduit 166 (by breaking the frangible closure) for pooling. This facility may be of any suitable configuration, but as one example may compress the tubing, such as by a roller or platen to detect for inadequate or leaking sterile connection.

For tracking the source, destination and processing of the blood or blood component, the system includes a controller and/or data collection module 172, which may be associated with the user interface 164. In one implementation or version, the user interface/data module may include a data display/input screen, and any suitable data input device such as a touch screen, keypad or other. The user interface could include a fixed or handheld scanner for reading data in barcode or other format such as RFID from the source containers. The user interface/data module may be configured for hardwire or WIFI connection to centralized data storage system or include a printer for printing labels with the appropriate information for attaching the destination or pooling container. Such information might include the blood or blood component pooled, blood type, date, equipment identification, operator identification and the like.

The basic pooling process has a limited number of steps, although these may be revised or supplemented as desired. The controller may be configured or programmed to display and/or lead the user through these steps, with appropriate user responses prompted as certain user manipulations or actions are completed. For example, the user may be required to enter a particular response via the interface after completion of a particular step. This same concept of controller configuration and prompting is not only applicable to the device of FIG. 7, but also the devices of FIGS. 3, 5 and 6. The steps generally include loading the blood or blood component source containers or bags; loading the pooling set or flow circuit; commencing the pooling process and removing the processing set. More detailed description of possible, non-limiting steps is set forth below.

Steps
1. Load blood component bag onto the suspension apparatus
   A. Scan container information into system
   B. Hang container onto suspension apparatus
   C. Load tubing into guides/rollers
2. Load pooling set onto a pooling set holder
   A. Scan pooling bag or container into system
   B. Hang pooling bag onto pooling set apparatus
   C. Load pooling tubing into guides/rollers
3. Start pooling process
   A. Sterile connect module slides across to each station and tubing guide and:
      i. Performs tubing check
      ii. Cartridge, wafer, tape, or blade, is loaded and prepared
      iii. Module slides to position/and performs sterile connection
      iv. Roller clamps test connection by pressure
      v. If connection is good, cannula breaker opens cannula to allow pooling.
         If connection is bad, cannula is not broken and tubing/bag Needs to be reloaded. System alerts user.
      vi. Steps iii to v are performed at each station.
4. Removal of Set
   A. Once sterile connect is completed and checks are satisfied, the user may select pooling complete prompt on screen.
   B. Sterile Connect Module:
      i. Slides to each position and seals tubing, and/or
      ii. Seals above pooled bag C. Screen Indicates Complete And
   i. Performs any last needed scans
   ii. Prints any needed labels or forms The present subject matter described above has a variety of features, aspects and implementations which may be claimed alone or in combination with other aspects or implementations.

Also, although the present subject matter has been described in connection with the drawings accompanying the description, it is understood that various changes or modifications may be apparent to one of ordinary skill upon reading this description and, accordingly, the scope of patent protection is as defined in the accompanying claims and not limited to the particular features or functions shown in the figures or described as set forth in the claims.

What is claimed is:

1. A blood collection system in a collection configuration comprising:
   a vascular access device for drawing blood from a donor or patient;
   a blood collection container including a blood inlet and having opposed ends, one end of the container including a first blood component outlet and the opposed end of the container including a second blood component outlet;
   a blood flow conduit extending between and in fluid communication with the access device and the blood inlet of then blood collection container, the blood collection container being free of attachment to other blood component collection containers receiving blood components from the collection container; and
   a tubing loop separate from the fluid flow conduit and having one end in fluid communication with the flow conduit and another end in fluid communication with the interior of the blood collection container, the tubing loop extending between the flow conduit at one end and the blood collection container at the other end.

2. The blood collection system of claim 1 wherein the tubing loop has a first end in communication with the flow conduit and a second and open end terminating within the blood collection container at a location spaced from the one end of the container.

3. The blood collection system of claim 1 in which the blood collection container includes a radiofrequency identification device.

4. A method of collecting one or more blood components from whole blood in a collection container of whole blood, the collection container including a blood connection inlet and opposed ends, one end of the container including a first blood component outlet and the opposed end of the container including a second blood component outlet, a tubing loop separate from the fluid flow conduit and having one end in fluid communication with the flow conduit and another end in fluid communication with the interior of the blood collection container, the tubing loop extending between the flow conduit at the one end and the blood collection container at the other end, the blood collection container being free of attachment to other blood component collection containers during the collecting, the method including:
   centrifuging the blood collection container sufficiently to separate the collected blood into at least a plasma component disposed toward the one end of the container and a concentrated red component disposed toward the other end of the container;
   sterilely connecting a plasma collection subassembly including a plasma collection container in fluid communication with the first blood component outlets and/or a red cell collection subassembly including a red cell collection container with the second of the blood component outlets; and
   expressing the plasma component and/or the concentrated red cell component from the collection container and into the respective subassembly.

5. The method of claim 4 including passing the concentrated red cell component into a processing container in the red cell collection subassembly, which processing container contains certain ingredients of a red blood cell preservative solution and then passing the concentrated red blood component and the certain ingredients into the red blood cell collection container containing other ingredients of the red cell preservative solution.

6. The method of claim 5, wherein the red cell collection subassembly includes a leukocyte reduction filter located in a flow path between the processing container and collection container and the method further comprises wetting filter media of the leukocyte reduction filter with the other ingredients of the red cell preservative solution before passing the concentrated red cell component and certain ingredients through the leukocyte reduction filter.

7. The method of claim 4 including drawing blood from a donor and conveying it through the blood collection inlet into the collection container and thereafter sealing the inlet.

8. The method of claim 4 wherein the whole blood collection container includes data storage media and the method includes reading the data from the data storage media of the whole blood collection container and transferring at least part of that data to data storage media associated with the red cell collection container and the plasma collection container.

9. The method of claim 8 wherein the data storage media comprises a label or a radiofrequency identification device.

10. The method of claim 4 including mixing certain ingredients of a red cell preservative solution contained in the red cell collection container with other ingredients of the red cell preservative solution contained in a separate container prior to introduction of red cells into the red cell collection container.

11. The method of claim 4 including filtering the red cells through a leukocyte reduction filter after the filter is wetted by at least a portion of a red cell preservative solution.

* * * * *